(12) United States Patent
Froman et al.

(10) Patent No.: US 7,715,913 B1
(45) Date of Patent: May 11, 2010

(54) EXTERNAL DEFIBRILLATOR WITH TRAINING MODE AND METHOD OF USE

(75) Inventors: James Adkins Froman, Issaquah, WA (US); Patrick Lee Hauge, Bellevue, WA (US); Hans Patrick Greisser, Bainbridge Island, WA (US); Daniel John Kingsbury, Seattle, WA (US); Douglas Michael Denney, Sammamish, WA (US); Ann Thom, Seattle, WA (US); Thomas Allen Solosko, Issaquah, WA (US); Thomas Dean Lyster, Bothell, WA (US); Kim Johnnie Hansen, Renton, WA (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 585 days.

(21) Appl. No.: 10/597,706

(22) PCT Filed: Jan. 31, 2005

(86) PCT No.: PCT/IB2005/050407

§ 371 (c)(1),
(2), (4) Date: Aug. 4, 2006

(87) PCT Pub. No.: WO2005/077455

PCT Pub. Date: Aug. 25, 2005

Related U.S. Application Data

(60) Provisional application No. 60/543,142, filed on Feb. 10, 2004.

(51) Int. Cl.
*A61N 1/00* (2006.01)
(52) U.S. Cl. ........................................ 607/5
(58) Field of Classification Search ............... 607/5, 607/2, 7, 10, 29; 128/897, 898
See application file for complete search history.

(56) References Cited

U.S. PATENT DOCUMENTS

| | | | |
|---|---|---|---|
| 5,137,458 A | 8/1992 | Ungs et al. | |
| 5,275,572 A * | 1/1994 | Ungs et al. | 434/265 |
| 5,611,815 A | 3/1997 | Cole et al. | |
| 5,662,690 A | 9/1997 | Cole et al. | |

(Continued)

FOREIGN PATENT DOCUMENTS

GB 2386071 A 9/2003

*Primary Examiner*—Mark W Bockelman
*Assistant Examiner*—Elizabeth K So
(74) *Attorney, Agent, or Firm*—W. Brinton Yorks, Jr.

(57) ABSTRACT

A method and apparatus for training a user to operate an external defibrillator, usable in a therapy or training mode, which includes an energy source; an electrode interface responsive to an electrode arrangeable on a release liner and configured for placement on a subject; and an energy delivery system operable to selectively deliver electrical energy from the energy source to the electrode via the electrode interface. The method includes: when the electrode is coupled to the electrode interface, receiving an input signal from the electrode, prior to placement of the electrode on the subject; based on the input signal, identifying a degree of electrical connectivity along an electrical path including the electrode; based on the determined degree of electrical conductivity, advancing the external defibrillator from a first training state to a second training state; and issuing a training state notification indicating advancement from the first training state to the second training state.

15 Claims, 5 Drawing Sheets

U.S. PATENT DOCUMENTS

| | | |
|---|---|---|
| 5,792,190 A | 8/1998 | Olson et al. |
| 5,993,219 A | 11/1999 | Bishay et al. |
| 2002/0143366 A1 | 10/2002 | Herleikson |
| 2003/0028219 A1 | 2/2003 | Powers et al. |
| 2003/0036044 A1 | 2/2003 | Pastrick et al. |
| 2003/0055478 A1 | 3/2003 | Lyster et al. |
| 2003/0199929 A1* | 10/2003 | Snyder et al. .................. 607/7 |
| 2003/0216785 A1 | 11/2003 | Edwards et al. |
| 2003/0233129 A1* | 12/2003 | Matos ........................... 607/5 |

* cited by examiner

EXTERNAL DEFIBRILLATOR WITH TRAINING MODE AND METHOD OF USE

CROSS REFERENCE TO RELATED APPLICATION

This application claims the benefit of U.S. provisional application Ser. no. 60/543,142 filed Feb. 10, 2004, which is incorporated herein.

Aspects of this invention relate generally to external defibrillator training, and more specifically to external defibrillators usable in a training mode and to a method for training a user to operate an external defibrillator.

Abnormal heart activity, such as ventricular fibrillation, may be returned to a normal sinus rhythm by applying an electric current to the heart using an external defibrillator. External defibrillators may be manual, automatic or semi-automatic. It is desirable to teach operators of all types of external defibrillators to use actual defibrillation equipment, in a realistic training environment that simulates and approximates actual defibrillator use procedures and conditions.

Modern external defibrillators may incorporate a training mode in addition to a therapy mode in order to provide an in situ training opportunity to potential users. In the therapy mode, electrotherapy is delivered from the defibrillator through medical electrodes attached to living subjects. In the training mode, electrotherapy is simulated—the training electrodes are attached to a training apparatus, such as a mannequin, and are not electrically connected to the defibrillator. Examples of external defibrillators having both therapy modes and training modes are provided in U.S. Pat. No. 5,611,815, and in U.S. Pat. No. 5,662,690, the specifications of which are incorporated herein by reference.

Interactive training modes of known defibrillators guide an operator through the defibrillation process without feedback from the training electrodes. Instead, the operational state changes in the defibrillator are simulated based on other inputs, such as elapsed time, detecting the insertion of a training electrode into an electrode interface, manipulation of the defibrillator controls by the user, or by signals generated by a remote device operated by the training supervisor. Interactive training generally begins with the operator being instructed to call emergency medical services, expose the chest, open and place one or more non-conductive training electrodes onto a particular position on a mannequin. The operator's proper electrode placement and positioning generally triggers an operational state change in the training mode of the defibrillator—the defibrillator operator, for example, next being instructed that the defibrillator is analyzing, and not to touch the patient. Actual medical electrodes, however, are often internally electrically conductive, to allow for communication with the defibrillator about electrode state or handling prior to patient placement, and may be packaged in containers and/or disposed on release liners, which must be successfully removed by a defibrillator operator prior to patient placement.

Several types of sensing systems have been developed to indicate proper positioning of training electrodes on mannequins. For example, conductive adapter strips for use with mannequins are described in U.S. Pat. No. 5,993,219. In another example, conductive objects are embedded in mannequins. In a further example, U.S. Pat. No. 5,137,458 describes mannequins fitted with Hall-effect sensors to detect magnetic fields produced by permanent magnets in training electrodes. Mannequins adapted for training electrode placement and detection, however, are expensive, complex, and/or impractical for many training applications and locations.

There is therefore a need for an external defibrillator having a training mode, and a method of operating an external defibrillator in the training mode, which interactively guides a defibrillator operator through pre-patient-placement electrode handling steps in a way that more closely approximates actual defibrillator procedures and conditions, and which may be used with more realistic training electrodes. There is also a need for a simple, low-cost, realistic training apparatus and method for use with an external defibrillator that allows for verification of proper electrode placement, but that does not require a mannequin.

According to one aspect of the present invention, an external defibrillator is selectably usable in one of a therapy mode and a training mode. When in the training mode, the defibrillator has a plurality of training state notifications. The defibrillator is adapted for electrical coupling with an electrode arrangeable on a release liner. The electrode is electrically conductive and configured for placement on a subject. The defibrillator includes an energy source; an electrode interface responsive to the electrode; an energy delivery system operable to selectively deliver electrical energy from the energy source to the electrode via the electrode interface; a state identifier, identifying, when the electrode is electrically coupled to the electrode interface, a degree of electrical connectivity along an electrical path including the electrode; a controller, operative in the training mode, prior to placement of the electrode on the subject, to advance the external defibrillator from a first training state to a second training state when the state identifier identifies a predetermined degree of electrical conductivity along the electrical path; and a user interface, operative in the training mode to issue a training state notification indicating that the external defibrillator has advanced from the first training state to the second training state.

The predetermined degree of electrical conductivity may be an impedance level, of between about 2000 ohms and 15K ohms, indicating that the electrode was removed from the release liner, or may alternatively indicate that the electrode was removed from a package containing the electrodes and release liner. The training state notification may be a voice message or visual prompt, instructing the user of subsequent actions to be taken. When the electrode is a training electrode, the training electrode includes a conductive attachment layer, and a conductive metal layer, such as tin foil, in communication therewith, having a void therein that provides a nonconductive region. The electrical path is through the conductive attachment layer and the release liner. When the training electrode is attached, the defibrillator is not operable in the therapy mode.

According to another aspect of the present invention, a method for training a user to operate an external defibrillator, usable in a therapy or training mode, includes an energy source; an electrode interface responsive to an electrode arrangeable on a release liner and configured for placement on a subject; and an energy delivery system operable to selectively deliver electrical energy from the energy source to the electrode via the electrode interface. The method includes: when the electrode is coupled to the electrode interface, receiving an input signal from the electrode, prior to placement of the electrode on the subject; based on the input signal, identifying a degree of electrical connectivity along an electrical path including the electrode; based on the determined degree of electrical conductivity, advancing the external defibrillator from a first training state to a second training state; and issuing a training state notification indicating advancement from the first training state to the second training state. A computer-readable storage medium may be encoded with a computer program which, when loaded into a processor, is operative to perform the method.

According to a still further aspect of the present invention, a method for making a training apparatus for use with an external defibrillator, the external defibrillator responsive to a first electrode and a second electrode, includes: providing a transparent layer having a first electrode attachment region defining an opening sized to receive the first electrode; disposing a signal conductor proximate the first electrode attachment region, the signal conductor having a transfer path, the transfer path operable to provide communication between the first electrode and the second electrode, when the first electrode and the second electrode are disposed on the training apparatus; and providing a two-dimensional representation of an anterior portion of a defibrillation subject, identifiable through the transparent layer, having the first electrode attachment region arranged thereon in a manner that defines a preferred placement area of the first electrode on the defibrillation subject. A second electrode attachment region may be defined to receive the second electrode. When the first and second electrodes are arranged in their respective attachment regions, in such a manner that the transfer path is operating, the external defibrillator is operable to detect a connection state between the first and second electrodes and the training apparatus.

According to a further additional aspect of the present invention, a method for performing defibrillator training includes: providing an automatic external defibrillator training device; providing a pair of training electrodes in electrical communication with the training device; sensing an impedance between the pair of training electrodes; and advancing a training rescue based on the sensed impedance. The method may further include changing an operational mode of the defibrillator to a training mode based on the sensing step, and providing a defibrillator training apparatus with electrically coupled depictions of the proper position of each of the training electrodes.

Figure 1:
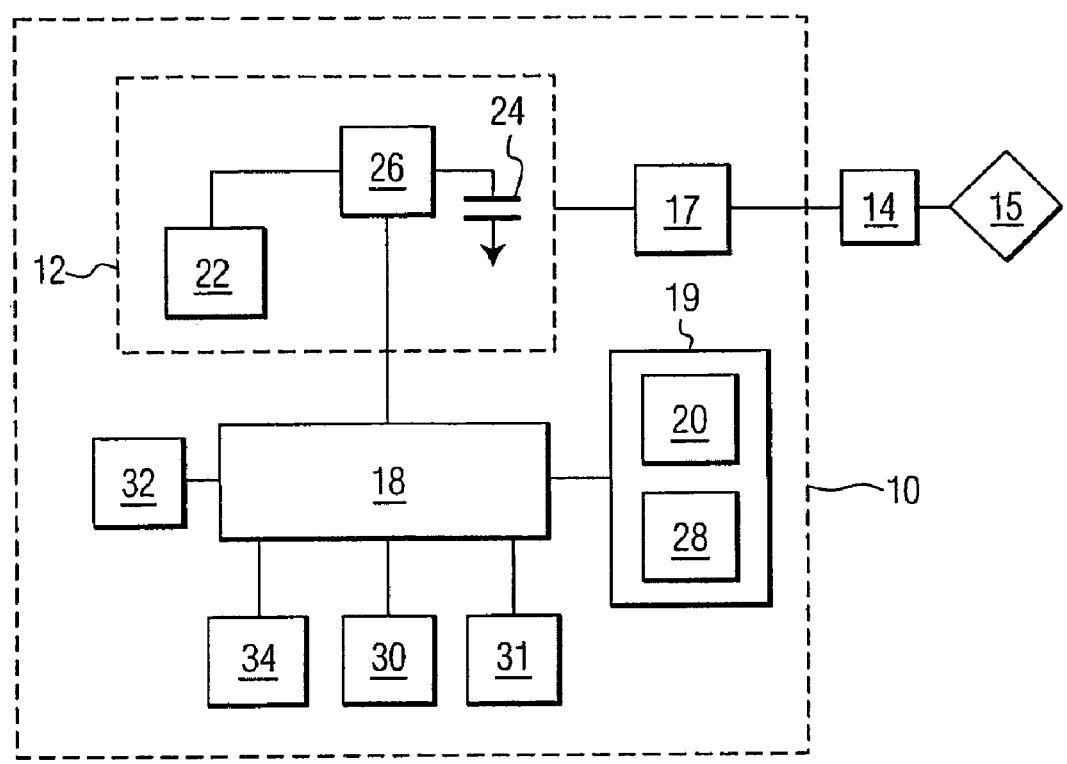
FIG. 1 is a schematic representation of an external defibrillator usable in connection with aspects of the present invention.

Turning now to the drawings, wherein like numerals designate like components, FIG. 1 is a schematic representation of an external defibrillator 10, suitable for use with aspects of the present invention. External defibrillator 10 may be automatic, semi-automatic, or manual, such as Philips Heartstart HS1. During normal operation, energy delivery system 12, under the control of controller 18, selectably provides actual or simulated voltage or current pulses using well-known methods and techniques to an electrode interface 17, via energy delivery system 12. Electrode interface 17 is detachably connectable to one or more electrodes 14, using, for example, a connector associated with electrode 14 or packaging (discussed further below) therefore. Defibrillator 10 is preferably adapted to use a variety of electrodes 14, including both treatment and training electrodes. Electrodes 14 are connected to defibrillation subjects 15, such as living persons or training apparatuses.

Energy delivery system 12 includes elements such as charging circuit 26, one or more capacitors 24, and an energy storage medium 22 (for example, a battery). Energy delivery system 12 also includes elements (not shown) such as electrical connectors, housings, signal conductors, or switches, to allow selectable connection of an energy source to electrode interface 17 by a controller 18.

Controller 18, which may be a processor, is illustrated functionally, and is responsive to various additional elements of defibrillator 10, including an operator interface 19, a memory 30, computer programs 31, a mode selector 32, and a state identifier 34.

Controller 18 receives input and provides output through operator interface 19, which, functionally, includes an input element 20 and an output element 28. Internal arrangements of input element 20 and output element 28 are well-known, and may include buttons or other actuators, displays, microphones, speakers, keypads, switches, status indicators, light-emitting diodes, temperature sensors, status measurement units, or other devices or ports, digital or analog, or any combination thereof.

Controller 18 is also responsive to memory 30, such as a removable data card, for storing digital and/or analog information. Memory 30 may be any local or remote computer-readable storage medium, now known or later developed, capable of storing data, including but not limited to a digital memory, a hard disk drive, a videocassette recorder tape, all types of compact disks and digital videodisks, a magnetic tape, or other local or networked storage means.

Controller 18 is further responsive to a state identifier 34, which may perform and/or direct periodic monitoring of various elements or systems of defibrillator 10, either automatically or in response to an operator's action. Internal arrangements of state identifier 34 are well known, and may include elements that characterize electrical or other communication paths, such as paths (discussed further below) internal to electrode(s) 14, or discriminate other operating conditions of defibrillator 10. State identifier 34 may perform in well known manners in conjunction with other elements of defibrillator 10, such as memory 30, controller 18, computer programs 31, mode selector 32, and operator interface 19. State identifier 34, for example, may operate in a manner set forth in U.S. Patent Application Publication No. US 2003/0055478, the disclosure of which is incorporated herein by reference.

Defibrillator 10 is preferably operable in at least two different modes—a treatment mode and training mode—selectable via mode selector 32. Mode selector 32 may be any suitable device or technique for changing the operational mode of defibrillator 10, such devices, techniques and operating principles thereof being well known. For example, insertion of a predetermined battery may cause defibrillator 10 to enter the training mode, or the training electrodes may be coded in a way that is differentiable and identifiable by the external defibrillator.

Figure 5:
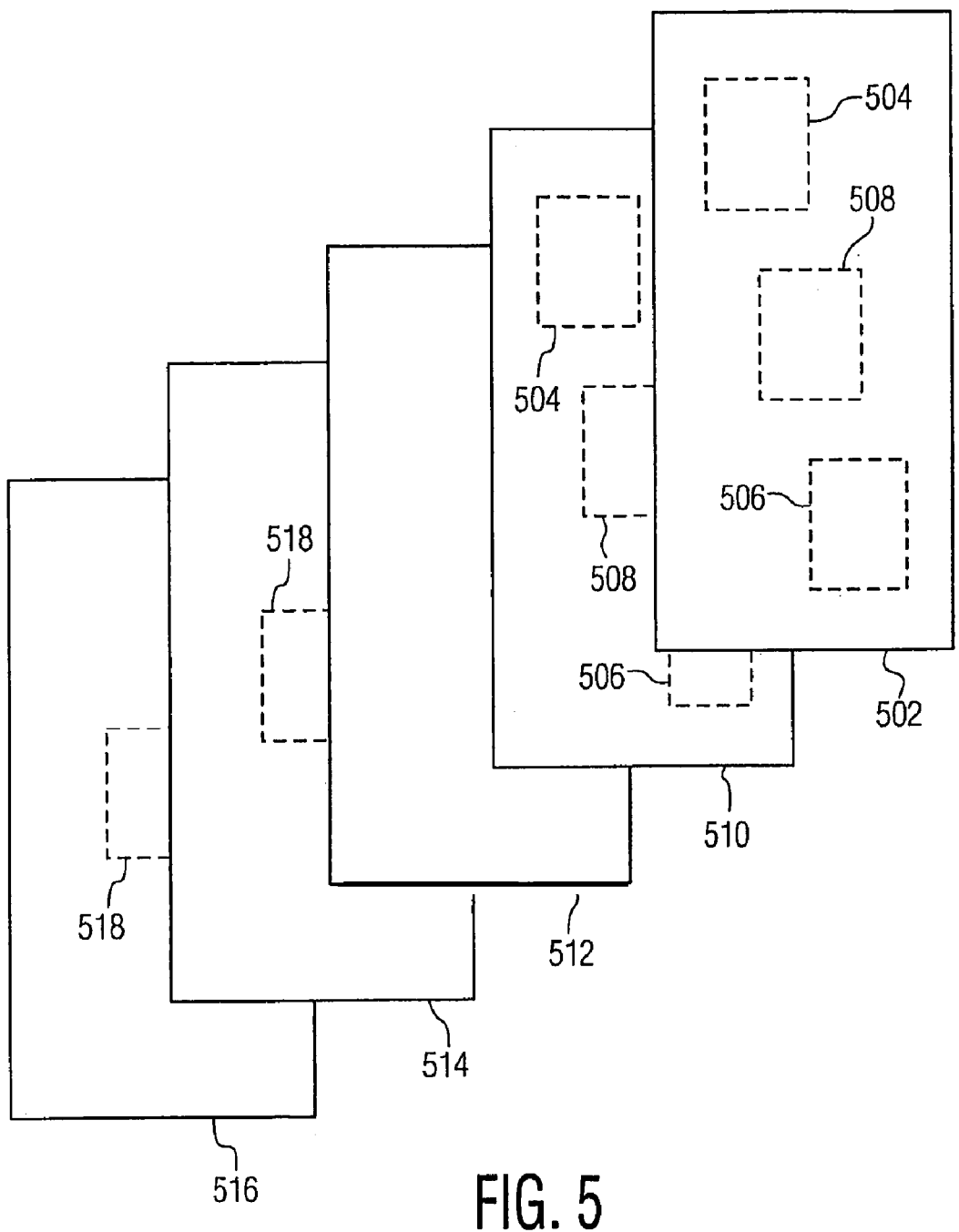
FIG. 5 is a layered perspective view of a training apparatus in accordance with aspects of the present invention.

In the treatment mode, currents are delivered through electrodes 14, such as medical electrodes, attached to living subjects. In the training mode, actual or simulated currents are delivered through electrodes 14, such as training electrodes 200 (shown in FIG. 2 and discussed further below), attached to a training apparatus (a training apparatus in accordance with further aspects of the present invention is shown in FIG. 5 and discussed further below). Once defibrillator 10 has entered the training mode, it is preferable that the external defibrillator is not operable in the therapy mode, and the operator may receive a notification, such as a voice prompt or other indicator, via operator interface 19, that defibrillator 10 is in the training mode.

One or more computer programs 31, alone or in combination with hardware or firmware, when loaded into a processor such as controller 18, are operative to control external defibrillator 10 in both therapy and training modes. Computer programs 31 may be stored in a memory, for example, memory 30. One skilled in the art may, using well known procedures and algorithms, select or implement instructions in software, hardware, firmware or a combination thereof, which effect operation and/or control of defibrillator 10 in the treatment and training modes.

Figure 2:
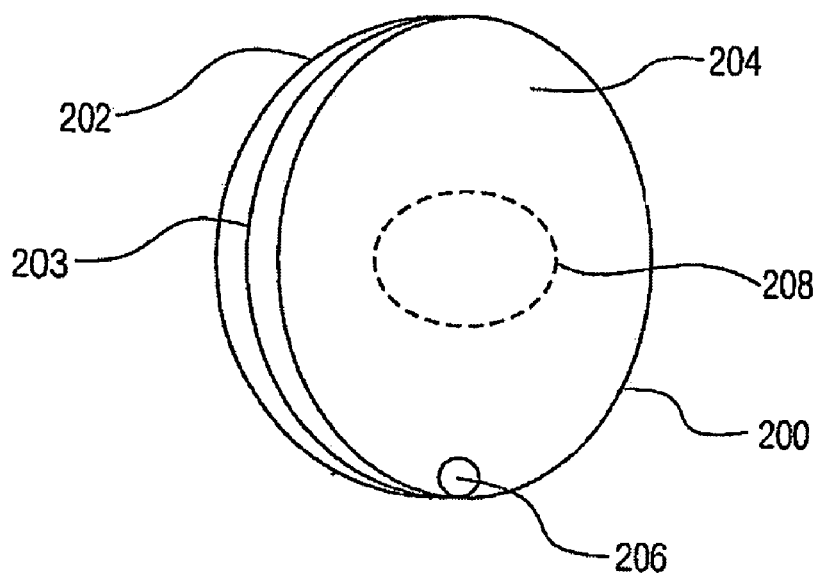
FIG. 2 illustrates a plan view of a training electrode usable in connection with aspects of the present invention.

In accordance with one aspect of the present invention, when defibrillator 10 is in the training mode, a training electrode, such as electrode 200 illustrated in plan view in FIG. 2, is electrically coupled and/or responsive to electrode interface 17. The training electrode is also preferably arranged in series with respect to defibrillator 10 with a resistive device 207, such as a resistor, having an impedance of approximately 1k ohms. Resistor 207 facilitates identification of electrode 200 as a training electrode, and not a therapy electrode, by raising the real component of the complex impedance level of the electrode above patient impedance levels, which are approximately 25-500 Ohms. Identification of electrode 200 as a training electrode may be important to prevent accidental shocking through electrode 200. Communication between electrode 200 and defibrillator 10 may occur via one or more communication paths such as a lead wire 206. This provides a safety feature. If the pads are mislabeled or not labeled, the defibrillator will not administer a high voltage shock.

As shown, electrode 200 is oval-shaped, although any suitable shape or combination of shapes is possible, such as a generally rectangular shape having curved edges. Electrode 200 preferably has a top side 202 (an edge thereof is shown), a bottom side 204, and an inner layer 203.

As is well-known, top side 202 may include an insulating, supportive, or protective cover (not shown), which may be flexible, and which may graphically indicate a proper placement of electrode 200 on a subject.

Bottom side 204 is preferably defined by a conductive attachment layer, such as a gel or adhesive layer, having an approximate thickness of about 0.020-0.040 inch (0.05-0.10 centimeter). A suitable conductive attachment layer is a hydrogel. A suitable hydrogel product is commercially available from Katecho, Inc. part number KM30G.

Internally, electrode 200 includes a conductive foil layer 203, interposed between top side 202 and bottom side 204. Conductive foil layer 203 preferably has an opening therein, such as a hole 208, of about 3.81 centimeters in diameter. Hole 208 may be cut, stamped or punched from conductive foil layer 203 using well-known methods and techniques. Hole 208 operates to provide a high level of pad-to-pad or pad-to-liner impedance when electrode 200 is disposed on one or either slide of the release liner. With two electrodes present, the gels make contact through the hole in the center of the liner.

Figure 3:
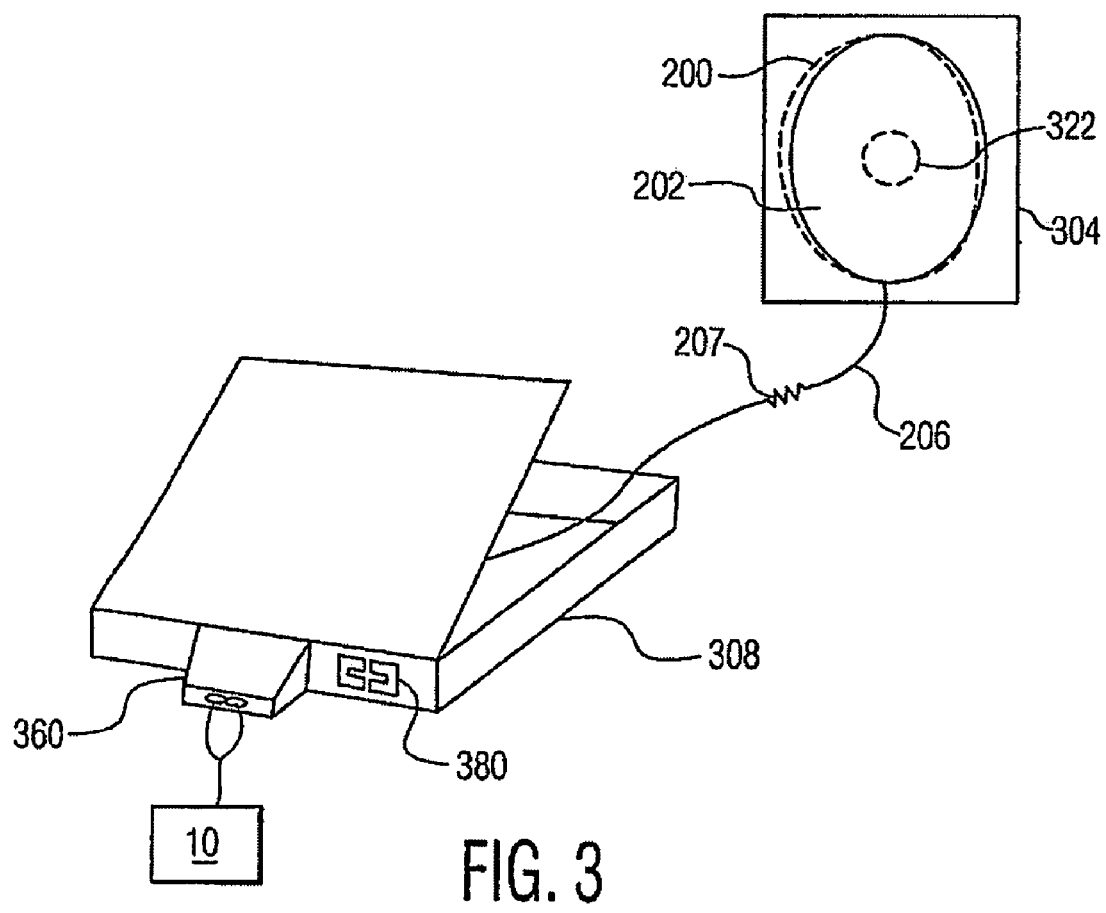
FIG. 3 is a perspective view of the training electrode shown in FIG. 2, mounted on a release liner and ready for storage in an electrode package.

In accordance with further aspects of the present invention, defibrillator 10 preferably operates in the training mode prior to placement of one or more training electrodes, such as electrodes 200, on a training subject. FIG. 3 is a perspective view of electrode 200 arranged on release liner 304, including optional further packaging 308.

Optional packaging 308 may comprise a housing having an electrical interface 360 for connection of electrodes, such as electrodes 200, to defibrillator 10. A cartridge identifier 380 may also be included in packaging 308, to facilitate identification of training electrodes by defibrillator 10. Package 308 may be implemented in any suitable manner.

Release liner 304 may be constructed of one or more layers of a nonconductive, non-stick material such as silicon-coated paper, polyester, polypropylene, polyethylene, and/or other non-stick material, in a manner well understood in the art. Release liner 304 preferably has an opening therein, such as a hole 322, of about 1.27 centimeters in diameter. Hole 322 may be cut, stamped or punched from release liner 304 using well-known methods and techniques. Examples of various release liner configurations adaptable for use in connection with aspects of the present invention are shown in U.S. Patent Application Publication US2003/005 5478, the specification of which is incorporated herein by reference.

Electrode 200 is preferably positioned on release liner 304 in such a manner that, when defibrillator 10 is electrically coupled to electrode 200, defibrillator 10 can characterize and/or identify a degree of electrical connectivity (for example, perform an impedance measurement to measure an impedance level) along an electrical path that includes electrode 200. It will be appreciated that the manner of electrically coupling electrode 200 to release liner 304 and/or defibrillator 10 may determine a number of characterizable electrical paths that include electrode 200.

As shown, bottom side 204 of electrode 200 is arranged on release liner 304, in such a manner that hole 208 (not visible) and the conductive attachment layer are disposed over hole 322. Lead wire 206, connected in series with resistor 207, is attachable to optional rigid electrode package 308. Electrical coupling between defibrillator 10 and electrode 200 may occur via connector 360, or, if package 308 is absent, via any other suitable connector.

One electrical path having an identifiable degree of electrical connectivity is created when the conductive attachment layer of electrode 200 is in contact with hole 322 in release liner 304, and electrode 200 is electrically coupled to defibrillator 10. In practice, the electrical path may include a second electrode (not shown, including the same elements as electrode 200), also arranged on release liner 304 in such a manner that its hole 208 and its conductive attachment layer are disposed over hole 322, such that the conductive attachment layers of both electrodes are in contact via hole 322. It will be appreciated that any arrangement of one or more electrodes on release liner 304 is possible, which allows defibrillator 10 to characterize a degree of electrical connectivity along an electrical path including one or more of the electrodes.

When package 308 is used, another electrical path having an identifiable degree of electrical connectivity may be created when electrode 200 (disposed on release liner 304) is stored in package 308, and package 308 is electrically coupled to defibrillator 10.

Referring now to FIGS. 1-3, during normal operation in the training mode, defibrillator 10 guides an operator through a training sequence that simulates operation of defibrillator 10 in the treatment mode. In accordance with one aspect of the present invention, when electrode interface 17 is electrically coupled to a training electrode such as electrode 200, and the training electrode is disposed on a release liner, such as release liner 304, but prior to the operator's placement of the training electrode on a training subject, defibrillator 10 is operative in a first training state. One possible first training state is waiting for the operator to remove the electrode from the release liner; another possible first training state is waiting for the operator to remove the electrode from other packaging, such as container 308. Defibrillator 10 advances from the first training state to a second training state when a predetermined degree of electrical connectivity or variability in the electrical conductivity occurs along an electrical path including the electrode. One example of the second training state is waiting for the operator to remove the electrode from a package, which causes a detectable change in pad-to-pad impedance. Another example of a second or third training state is waiting for the operator to remove one or more pads from the release liner. A further training state is to wait until the user properly places the electrode(s) onto a training apparatus. The operator of defibrillator 10 is notified by operator interface that defibrillator 10 has changed training states—a voice prompt, for example, may acknowledge the removal of one or more electrodes 200 from release liner 304, and/or instruct the operator to place the removed electrode(s) onto a training apparatus. Other prompts, such as blinking light(s) or text written to a display may also serve to notify the operator that defibrillator 10 has changed training states.

Training state advancement is preferably performed or coordinated by controller 18, and state identifier 34 preferably identifies the predetermined degree of electrical connectivity—by obtaining an impedance measurement along the electrical path, for example. The identified impedance may indicate that the operator has removed the training electrode from the release liner, and/or removed the release liner from any optional packaging. For example, in the case of two electrodes 200 attached to a common release liner 304, with the conductive attachment layers 204 of the electrodes in electrical contact via opening 322, an electrical current traveling through the conductive attachment layers would encounter a predetermined impedance associated with opening 322. An impedance in a range greater than about 2000 ohms, but less than about 15 Kohms indicates that one or both electrodes 200 remain on release liner 304, and no training state advancement occurs. An impedance indicating that one or both electrodes 200 have been removed from release liner 304 (for example, the impedance approaches infinity), triggers controller 18 to advance defibrillator 10 from the first training state to the second training state.

The removal of one or more electrodes 200 from any optional packaging may be detected by measuring small changes in electrode-to-electrode impedance. Upon handling the electrode pads, the pad-to-pad impedance experiences changes larger than the noise floor. The device monitors, identifies, and enhances these pad-to-pad impedance changes in order to detect when the pads have been removed from their package. When these impedance changes are detected, the defibrillator advances to the next training state or to the next training prompt.

Figure 4:
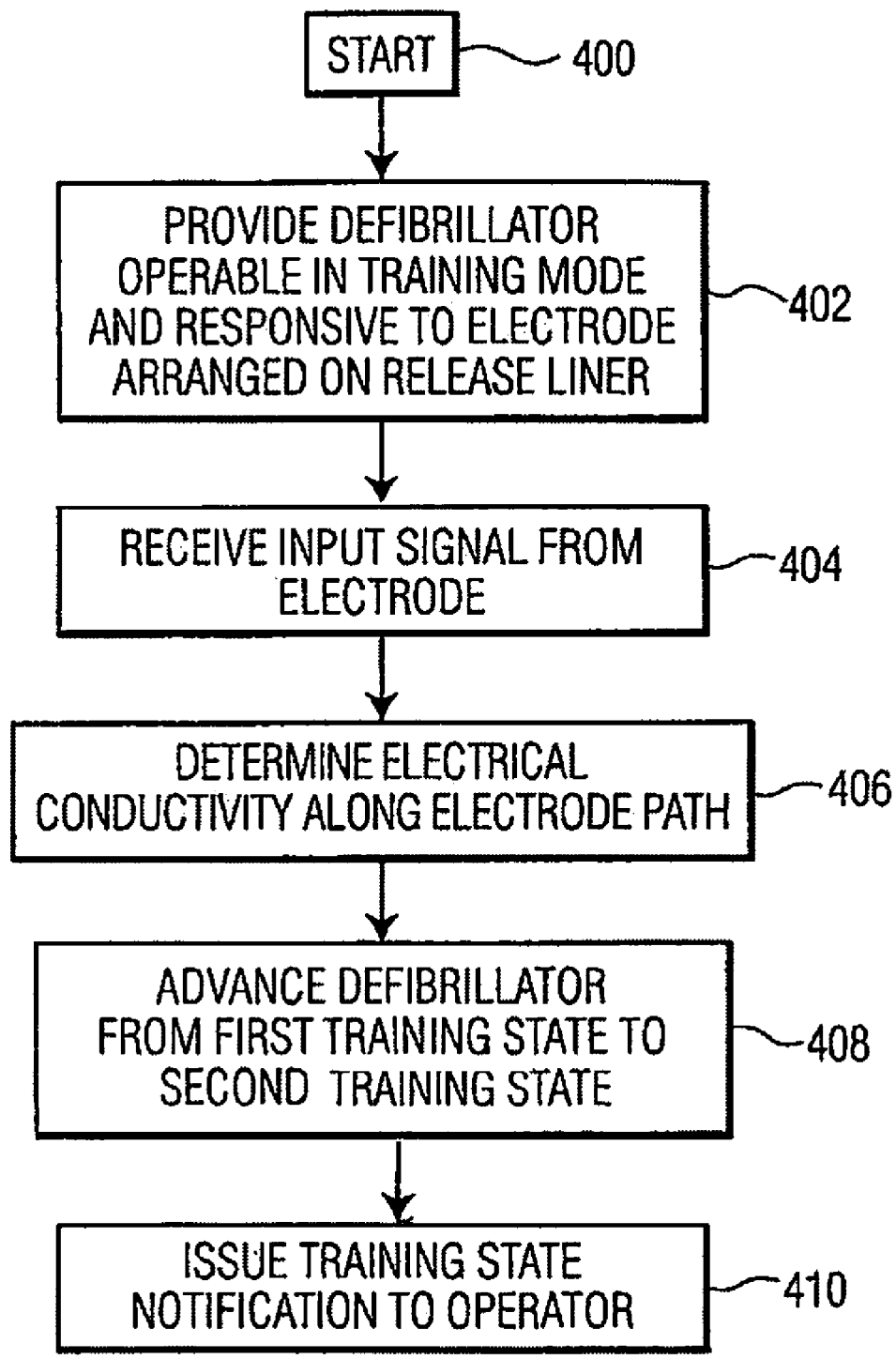
FIG. 4 is a flowchart of a method for training an operator to use the external defibrillator represented in FIG. 1.

In accordance with another aspect of the present invention, with continuing reference to FIGS. 1-3, a flowchart of a method for training an operator to use a defibrillator, such as defibrillator 10, is shown in FIG. 4. After beginning at block 400, at step 402, an external defibrillator, such as defibrillator 10, operable in both treatment and training modes and responsive to an electrode, such as electrode 200 coupled to electrode interface 17 and arranged on a release liner, such as release liner 304, is provided. The method continues at step 404, where an input signal is received from the electrode, prior to placement of the electrode on a subject such as a training apparatus. At step 406, a degree of electrical connectivity is determined along an electrical path that includes the electrode. For example, an impedance that indicates whether the conductive attachment layer of electrode 200 is in contact with opening 322 may be measured. Based on the determined degree of electrical connectivity, the external defibrillator may advance from a first training state (for example, waiting for an operator to remove the electrode from the release liner) to a second training state (for example, waiting for the operator to place the electrode on the training apparatus), at step 408. At step 410, a training state notification—a voice prompt, for example—is issued to the operator, indicating that the defibrillator advanced from the first training state to the second training state.

After a defibrillator operating in the training mode in accordance with above-described aspects of the present invention reaches a state where training electrodes coupled thereto have been removed from packaging and/or release liners, the training electrodes may be applied to a training apparatus.

In accordance with a further aspect of the present invention, FIG. 5 is a layered perspective view of a training apparatus 500 particularly useful with defibrillator 10 (shown in FIG. 1), and one or more training electrodes 200 (shown in FIG. 2). Apparatus 500 may, however, be adapted for use with any type of defibrillator or training electrodes.

With reference to FIG. 5, and also to FIGS. 1-3, apparatus 500 includes a transparent first layer 502. Layer 502 may be, for example, polyester or another clear material or coating of any suitable thickness in the range of about 0.001 to 0.010 inch (0.0025-0.25 cm) that allows for detachment of the conductive attachment layer of electrode 200. As shown, layer 502 (and subsequent layers, discussed further below) is rectangular, although any geometric shape is possible. Layer 502 preferably includes one or more, electrode attachment regions 504, 506 and 508, such as openings sized to receive electrodes 200. Three electrode attachment regions 504, 506 and 508 are shown, although in practice either one, two or three openings would be placed via die-cutting, punching, cutting, stamping or another suitable method or technique. Electrode attachment regions 504 and 506 are preferably located in areas (discussed further below) approximating proper placement of electrodes on the anterior torso of an adult defibrillation subject (also discussed further below), and electrode attachment region 508 is preferably located in an area approximating proper placement of an electrode on the anterior torso of a child defibrillation subject. Electrode attachment regions may be smaller or larger than the size of electrodes adapted for attachment thereto.

Figure 6:
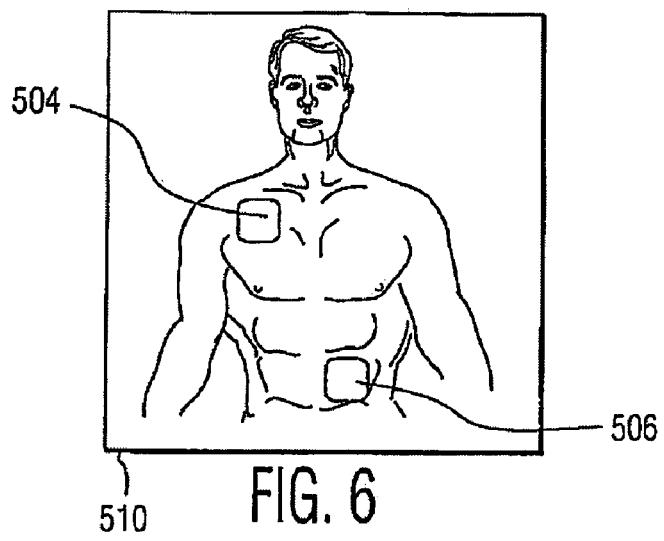
FIG. 6 is a plan view of one configuration of a certain layer of the training apparatus shown in FIG. 5.
Figure 7:
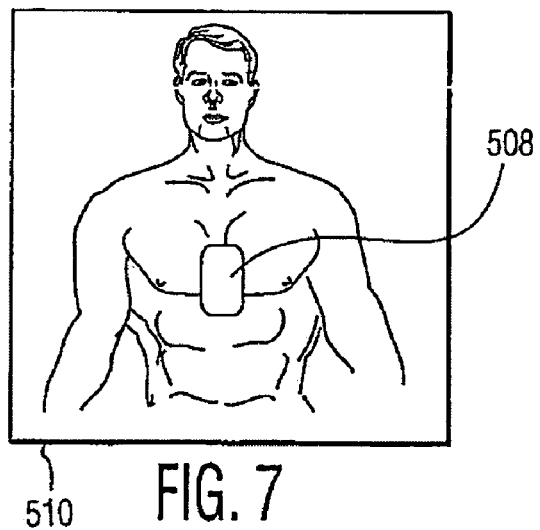
FIG. 7 is a plan view of another configuration of the layer shown in FIG. 6.

A second layer 510 is a two-dimensional representation of an anterior portion of a defibrillation subject, either an adult's torso or a child's torso, identifiable through transparent first layer 502. Layer 510 may be a printable paper or label. FIG. 6 is an example of second layer 510 having an adult's torso shown thereon. The adult's torso may be life-sized, or another size. FIG. 7 is an example of second layer 510 having a torso shown thereon with an electrode attachment region 508 in the center of the sternum. The torso may be life-sized, or another size. Layer 510 also preferably includes openings therein, sized and positioned similarly to openings 504, 506 and 508 in layer 502. As shown in FIG. 6, openings 504 and 506 are arranged in the sternum and apex positions, respectively, of the adult's torso, and the apex position may be graphically indicated to wrap around the torso. FIG. 7 illustrates opening 508 arranged in approximately the middle of the torso.

Referring again to FIG. 5, and to FIGS. 1-3 as necessary, a third layer 512 is a signal conductor. Layer 512 operates to provide a communication path, such as an electrical path, between two electrodes, such as electrodes 200, when they are properly positioned in electrode attachment regions 504 and 506, or 508 and 518 (discussed further below). When electrodes 200 are properly placed on appropriate electrode attachment regions, defibrillator 10 may detect a predetermined degree of impedance (for example, an impedance associated with opening 208) across the electrical path between the electrodes—and may interact with the operator of defibrillator 10 in the training mode based on the impedance detection in accordance with well-known methods and techniques.

Layer 512 may be pure grade tin or another conductive material that does not corrode in the presence of the conductive attachment layer of electrode 200, and may be exposed through attachment regions/openings 504, 506 and 508. As shown, layer 512 is co-extensive with layer 510 and 514 (discussed further below), but may have a different configuration, such as a smaller length or width that still extends from one electrode attachment region to another. Alternatively, signal conduction may occur via networked individual conductors within or about electrode attachment regions 504 and 506, or 508 and 518 (discussed further below). If layer 510 represents an adult's torso, and both electrode attachment regions 504 and 506 are formed on layer 502, then layer 512 may be laminated on one side (for example, on the side opposite layer 502), with polyester or another suitable material. If layer 510 represents a child's torso, then layer 512 may additionally be folded (for example, in half), so that a conductive side is positioned in two directions—one direction facing layer 502, and another direction facing a fourth layer 514. Layer 512 is foldable or bendable in a way that minimizes the number of folds through the signal conductor.

Figure 8:
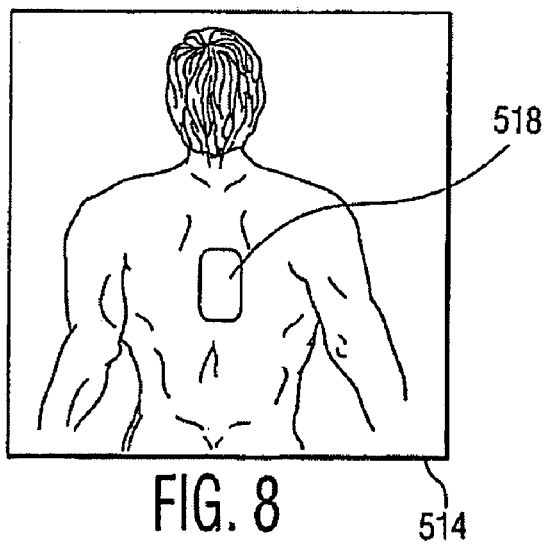
FIG. 8 is a plan view of another layer of the training apparatus shown in FIG. 5.

Fourth layer 514 protects third layer 512. When layer 510 represents an adult's torso, layer 514 may be a plain paper layer, or another non-conductive material, and may serve as the back of apparatus 500. It may also be printed to show the two-dimensional representation of the adult back or posterior view for times when posterior electrode placement training is requisite, as illustrated in FIG. 8. When layer 510 represents a child's torso, layer 514 is preferably a two-dimensional representation of a posterior view of the child's torso, identifiable through a transparent fifth layer 516, which is configured and constructed in the same manner as layer 502, including an electrode attachment region 518 that may be offset from electrode attachment region 508.

The embodiment(s) depicted and described herein are meant to be illustrative in nature, and it will be understood that various training apparatuses, methods, systems and defibrillators may be designed using the principles set forth herein, and used for various commercial and consumer applications. For example, it will be appreciated that aspects of the present invention are not limited to any specific embodiments of computer programs or signal processing methods, and that multiple storage media, controllers/processors and configurations of such devices are possible. Moreover, the methods described herein may be implemented by computer software, firmware, hardware (e.g., application-specific integrated circuits), or any combination thereof.

The invention claimed is:

1. An external defibrillator selectably usable in one of a therapy mode and a training mode, when in the training mode, having a plurality of training state notifications, and adapted for electrical coupling with an electrode arrangeable on a release liner, the electrode electrically conductive and configured for placement on a subject, comprising:
    an energy source;
    an electrode interface responsive to the electrode;
    an energy delivery system operable to selectively deliver electrical energy from the energy source to the electrode via the electrode interface;
    a state identifier, identifying, when the electrode is electrically coupled to the electrode interface, a degree of electrical connectivity along an electrical path including the electrode;
    a controller, operative in the training mode, prior to placement of the electrode on the subject, to advance the external defibrillator from a first training state to a second training state when the state identifier identifies a predetermined degree of electrical conductivity along the electrical path; and
    a user interface, operative in the training mode to issue a training state notification indicating that the external defibrillator has advanced from the first training state to the second training state.

2. The external defibrillator according to claim 1, wherein the predetermined degree of electrical conductivity comprises an impedance level.

3. The external defibrillator according to claim 2, wherein the impedance level indicates that the electrode was removed from the release liner.

4. The external defibrillator according to claim 2, wherein the predetermined degree of electrical conductivity indicates that the electrode was removed from a package containing the electrode attached to the release liner.

5. The external defibrillator according to claim 1, wherein the training state notification comprises one of a voice message and a visual prompt.

6. The external defibrillator according to claim 5, wherein the voice message comprises one of a message instructing a user to remove the electrode from the release liner and a message instructing a user to place the electrode on a training apparatus.

7. The external defibrillator according to claim 1, wherein the training mode is selected based on identification of the electrical coupling of the external defibrillator with a training electrode.

8. The external defibrillator according to claim 7, wherein the training electrode comprises:
    a conductive attachment layer; and
    a conductive metal layer in communication with the conductive attachment layer, the conductive metal layer having a void therein that provides a nonconductive region within the conductive metal layer.

9. The external defibrillator according to claim 8, wherein the electrical path comprises a path through the conductive attachment layer and the release liner.

10. The external defibrillator according to claim 7, wherein the identification of the training electrode is based on an impedance associated with the training electrode.

11. The external defibrillator according to claim 10, wherein the impedance level of the training electrode is based on a resistance value of a resistor coupled in series with the training electrode.

12. The external defibrillator according to claim 7, wherein when the training electrode is attached, the external defibrillator is not operable in the therapy mode.

13. The external defibrillator according to claim 1, wherein, when the defibrillator is in the therapy mode, the subject comprises a human being and, when the defibrillator is in the training mode, the subject comprises a training apparatus.

14. The external defibrillator according to claim 13, wherein the training apparatus comprises:
    a layer having an electrode attachment region defining an area sized to receive the electrode;
    a signal conductor disposed proximate the electrode attachment region, the signal conductor operable to provide communication between the electrode and the external defibrillator when the electrode is disposed on the electrode attachment region; and a two-dimensional representation of a subject having the electrode attachment region arranged thereon in a manner that defines a preferred placement area of the electrode on the subject.

15. A method for training a user to operate an external defibrillator, comprising:

providing an external defibrillator selectably usable in one of a therapy mode and a training mode, the external defibrillator comprising:

an energy source;

an electrode interface responsive to an electrode, the electrode arrangeable on a release liner and configured for placement on a subject; and an energy delivery system operable to selectively deliver electrical energy from the energy source to the electrode via the electrode interface;

when the electrode is coupled to the electrode interface, receiving an input signal from the electrode, prior to placement of the electrode on the subject;

based on the input signal, identifying a degree of electrical connectivity along an electrical path including the electrode;

based on the determined degree of electrical conductivity, advancing the external defibrillator from a first training state to a second training state and issuing a training state notification indicating advancement from the first training state to the second training state.

* * * * *

UNITED STATES PATENT AND TRADEMARK OFFICE
CERTIFICATE OF CORRECTION

PATENT NO. : 7,715,913 B1  Page 1 of 1
APPLICATION NO. : 10/597706
DATED : May 11, 2010
INVENTOR(S) : Froman et al.

It is certified that error appears in the above-identified patent and that said Letters Patent is hereby corrected as shown below:

On the front page of the issued patent, kindly correct the spelling of the last name of two inventors in the Inventors Bibliographic Data field (75), as follows:

Kindly correct the name "Ann Thom" to read --Ann Thorn--, such that the last name has 5 letters ending in r and n.

Kindly correct the name "Hans Patrick Greisser" to read --Hans Patrick Griesser--.

Signed and Sealed this

Twenty-eighth Day of September, 2010

David J. Kappos
*Director of the United States Patent and Trademark Office*